(12) United States Patent
Chappa et al.

(10) Patent No.: US 9,364,349 B2
(45) Date of Patent: Jun. 14, 2016

(54) COATING APPLICATION SYSTEM WITH SHAPED MANDREL

(75) Inventors: Ralph A. Chappa, Ham Lake, MN (US); James H. Arps, Chanhassen, MN (US)

(73) Assignee: SurModics, Inc., Eden Prairie, MN (US)

( * ) Notice: Subject to any disclaimer, the term of this patent is extended or adjusted under 35 U.S.C. 154(b) by 1943 days.

(21) Appl. No.: 12/109,139

(22) Filed: Apr. 24, 2008

(65) Prior Publication Data

US 2009/0269481 A1    Oct. 29, 2009

(51) Int. Cl.
*A61F 2/82* (2013.01)
*B05B 13/04* (2006.01)
*B05B 13/02* (2006.01)

(52) U.S. Cl.
CPC ............... *A61F 2/82* (2013.01); *B05B 13/0442* (2013.01); *A61F 2240/001* (2013.01); *B05B 13/0242* (2013.01)

(58) Field of Classification Search
USPC ................. 427/421, 2.25, 2.24, 2.26, 3, 358; 623/1.22
See application file for complete search history.

(56) References Cited

U.S. PATENT DOCUMENTS

| | | |
|---|---|---|
| 1,281,672 A | 10/1918 | Schorn |
| 1,866,100 A | 7/1932 | Hach |
| 2,253,019 A | 8/1941 | Crepeau |
| 2,330,880 A | 10/1943 | Gladfelter et al. |
| 2,493,787 A | 1/1950 | Torretti |
| 2,781,280 A | 2/1957 | Miller |
| 3,198,170 A | 8/1965 | Toshio |
| 3,318,281 A | 5/1967 | Plegat |
| 3,935,896 A | 2/1976 | Tegtmeier et al. |
| 3,963,069 A | 6/1976 | Marti et al. |
| 4,051,805 A | 10/1977 | Waldrum |
| 4,060,116 A | 11/1977 | Frailly |
| 4,073,335 A | 2/1978 | Fort et al. |
| 4,075,975 A | 2/1978 | Oswald |
| 4,153,201 A | 5/1979 | Berger et al. |
| 4,174,678 A | 11/1979 | Van Den Bergh |
| 4,195,637 A | 4/1980 | Gruntzig et al. |

(Continued)

FOREIGN PATENT DOCUMENTS

| | | |
|---|---|---|
| CA | 2351016 | 12/2001 |
| DE | 3335502 | 3/1985 |

(Continued)

OTHER PUBLICATIONS

PCT International Search Report and Written Opinion from International Application No. PCT/US2009/041575, corresponding to U.S. Appl. No. 12/109,139, mailed Jul. 22, 2009, pp. 1-15.

(Continued)

*Primary Examiner* — Andrew Bowman
(74) *Attorney, Agent, or Firm* — Pauly, DeVries, Smith & Deffner, L.L.C.

(57) ABSTRACT

The invention relates to systems and methods for applying coatings to devices. In an embodiment, the invention includes a coating apparatus including a mandrel having a lengthwise axis and an exterior surface, the exterior surface of the mandrel defining a plurality of channels disposed parallel to the lengthwise axis, the mandrel configured to rotate around the lengthwise axis; and a spray head configured to direct a stream of material at the mandrel. In an embodiment the invention includes a method of applying a coating to a medical device. Other embodiments are also included herein.

16 Claims, 9 Drawing Sheets

(56) References Cited

U.S. PATENT DOCUMENTS

| | | |
|---|---|---|
| 4,240,373 A | 12/1980 | Anger |
| 4,289,089 A | 9/1981 | Tacke et al. |
| 4,301,968 A | 11/1981 | Berger et al. |
| 4,337,896 A | 7/1982 | Berger et al. |
| 4,352,459 A | 10/1982 | Berger et al. |
| 4,375,820 A | 3/1983 | Vinarcsik et al. |
| 4,503,802 A | 3/1985 | Keller et al. |
| 4,541,564 A | 9/1985 | Berger et al. |
| 4,567,934 A | 2/1986 | Nakao et al. |
| 4,572,451 A | 2/1986 | Ikeda et al. |
| 4,638,045 A | 1/1987 | Kohn et al. |
| 4,655,393 A | 4/1987 | Berger |
| 4,723,708 A | 2/1988 | Berger et al. |
| 4,743,252 A | 5/1988 | Martin, Jr. et al. |
| 4,978,067 A | 12/1990 | Berger et al. |
| 5,041,089 A | 8/1991 | Mueller et al. |
| 5,087,246 A | 2/1992 | Smith |
| 5,102,402 A | 4/1992 | Dror et al. |
| 5,183,509 A | 2/1993 | Brown et al. |
| 5,219,120 A | 6/1993 | Ehrenberg et al. |
| 5,304,121 A | 4/1994 | Sahatjian |
| 5,318,587 A | 6/1994 | Davey |
| 5,382,234 A | 1/1995 | Cornelius et al. |
| 5,387,247 A | 2/1995 | Vallana et al. |
| 5,413,638 A | 5/1995 | Bernstein, Jr. et al. |
| 5,501,735 A | 3/1996 | Pender |
| 5,527,389 A | 6/1996 | Rosenblum et al. |
| 5,571,089 A | 11/1996 | Crocker |
| 5,643,362 A | 7/1997 | Garves |
| 5,656,332 A | 8/1997 | Saito et al. |
| 5,658,387 A | 8/1997 | Reardon et al. |
| 5,743,964 A | 4/1998 | Pankake |
| 5,776,101 A | 7/1998 | Goy |
| 5,807,331 A | 9/1998 | Den Heijer et al. |
| 5,833,891 A | 11/1998 | Subramaniam et al. |
| 5,837,008 A | 11/1998 | Berg et al. |
| 5,837,088 A | 11/1998 | Palmgren et al. |
| 5,882,336 A | 3/1999 | Janacek |
| 5,882,405 A | 3/1999 | Kish et al. |
| 5,897,911 A | 4/1999 | Loeffler |
| 6,019,784 A | 2/2000 | Hines |
| 6,153,252 A | 11/2000 | Hossainy et al. |
| 6,156,373 A | 12/2000 | Zhong et al. |
| 6,203,551 B1 | 3/2001 | Wu |
| 6,203,732 B1 | 3/2001 | Clubb et al. |
| 6,245,099 B1 | 6/2001 | Edwin et al. |
| 6,254,921 B1 | 7/2001 | Chappa et al. |
| 6,322,847 B1 | 11/2001 | Zhong et al. |
| 6,333,595 B1 | 12/2001 | Horikawa et al. |
| 6,345,630 B2 | 2/2002 | Fishkin et al. |
| 6,358,556 B1 | 3/2002 | Ding et al. |
| 6,368,658 B1 | 4/2002 | Schwarz et al. |
| 6,394,995 B1 | 5/2002 | Solar et al. |
| 6,395,326 B1 | 5/2002 | Castro et al. |
| 6,406,754 B2 | 6/2002 | Chappa et al. |
| 6,431,770 B1 | 8/2002 | Kurematsu et al. |
| 6,435,959 B1 | 8/2002 | Skrmetta |
| 6,506,437 B1 | 1/2003 | Harish et al. |
| 6,517,515 B1 | 2/2003 | Eidenschink |
| 6,517,889 B1 | 2/2003 | Jayaraman |
| 6,521,299 B1 | 2/2003 | Dessauer |
| 6,527,863 B1 | 3/2003 | Pacetti et al. |
| 6,544,582 B1 | 4/2003 | Yoe |
| 6,555,157 B1 | 4/2003 | Hossainy |
| 6,562,136 B1 | 5/2003 | Chappa et al. |
| 6,565,659 B1 | 5/2003 | Pacetti et al. |
| 6,572,644 B1 | 6/2003 | Moein |
| 6,605,154 B1 | 8/2003 | Villareal |
| 6,607,598 B2 | 8/2003 | Schwarz et al. |
| 6,616,765 B1 | 9/2003 | Castro et al. |
| 6,623,504 B2 | 9/2003 | Vrba et al. |
| 6,656,529 B1 | 12/2003 | Pankake |
| 6,669,980 B2 | 12/2003 | Hansen |
| 6,673,154 B1 | 1/2004 | Pacetti et al. |
| 6,676,987 B2 | 1/2004 | Zhong et al. |
| 6,695,920 B1 | 2/2004 | Pacetti et al. |
| 6,709,514 B1 | 3/2004 | Hossainy |
| 6,709,712 B2 | 3/2004 | Chappa et al. |
| 6,723,373 B1 | 4/2004 | Narayanan et al. |
| 6,725,901 B1 | 4/2004 | Kramer et al. |
| 6,743,462 B1 | 6/2004 | Pacetti |
| 6,743,463 B2 | 6/2004 | Weber et al. |
| 6,783,793 B1 | 8/2004 | Hossainy et al. |
| 6,803,070 B2 | 10/2004 | Weber |
| 6,818,063 B1 | 11/2004 | Kerrigan |
| 6,896,842 B1 | 5/2005 | Hamilton et al. |
| 6,981,982 B2 | 1/2006 | Armstrong et al. |
| 7,010,933 B2 | 3/2006 | Ishitomi et al. |
| 7,045,015 B2 | 5/2006 | Renn et al. |
| 7,125,577 B2 | 10/2006 | Chappa |
| 7,163,523 B2 | 1/2007 | Devens, Jr. et al. |
| 7,192,484 B2 | 3/2007 | Chappa et al. |
| 7,198,675 B2 | 4/2007 | Fox et al. |
| 7,335,314 B2 | 2/2008 | Wu |
| 7,563,324 B1 | 7/2009 | Chen et al. |
| 7,611,532 B2 | 11/2009 | Bates et al. |
| 7,669,548 B2 | 3/2010 | Chappa |
| 7,958,840 B2 | 6/2011 | Chappa |
| 8,003,156 B2 | 8/2011 | Van Sciver |
| 8,632,837 B2 | 1/2014 | Gong et al. |
| 2001/0001824 A1 | 5/2001 | Wu |
| 2002/0051730 A1 | 5/2002 | Bodnar et al. |
| 2002/0082679 A1* | 6/2002 | Sirhan et al. ............... 623/1.15 |
| 2002/0094440 A1 | 7/2002 | Llanos et al. |
| 2002/0103526 A1 | 8/2002 | Steinke |
| 2002/0115400 A1 | 8/2002 | Skrmetta |
| 2002/0155212 A1 | 10/2002 | Hossainy |
| 2003/0003221 A1 | 1/2003 | Zhong et al. |
| 2003/0044514 A1 | 3/2003 | Richard |
| 2003/0054090 A1 | 3/2003 | Hansen |
| 2003/0059520 A1 | 3/2003 | Chen et al. |
| 2003/0059920 A1 | 3/2003 | Drohan et al. |
| 2003/0088307 A1 | 5/2003 | Shulze et al. |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0190420 A1 | 10/2003 | Chappa et al. |
| 2004/0062875 A1* | 4/2004 | Chappa et al. ............... 427/421 |
| 2004/0073298 A1 | 4/2004 | Hossainy |
| 2004/0081745 A1 | 4/2004 | Hansen |
| 2004/0161547 A1 | 8/2004 | Carlson et al. |
| 2004/0185168 A1 | 9/2004 | Weber et al. |
| 2004/0194704 A1 | 10/2004 | Chappa et al. |
| 2004/0213893 A1 | 10/2004 | Boulais |
| 2005/0098097 A1 | 5/2005 | Chen et al. |
| 2005/0142070 A1 | 6/2005 | Hartley |
| 2005/0158449 A1 | 7/2005 | Chappa |
| 2006/0020295 A1 | 1/2006 | Brockway et al. |
| 2006/0029720 A1* | 2/2006 | Panos et al. ............... 427/2.1 |
| 2006/0045981 A1 | 3/2006 | Tsushi et al. |
| 2006/0064134 A1 | 3/2006 | Mazar et al. |
| 2006/0064142 A1 | 3/2006 | Chavan et al. |
| 2006/0074404 A1 | 4/2006 | Struble |
| 2006/0088653 A1 | 4/2006 | Chappa |
| 2006/0096535 A1 | 5/2006 | Haller et al. |
| 2006/0111754 A1 | 5/2006 | Rezai et al. |
| 2006/0116590 A1 | 6/2006 | Fayram et al. |
| 2006/0165872 A1 | 7/2006 | Chappa et al. |
| 2006/0191476 A1 | 8/2006 | Nagase et al. |
| 2007/0101933 A1 | 5/2007 | Chappa |
| 2007/0116855 A1 | 5/2007 | Fox et al. |
| 2007/0131165 A1 | 6/2007 | Fox et al. |
| 2007/0141232 A1 | 6/2007 | Tochterman et al. |
| 2007/0259100 A1 | 11/2007 | Guerriero et al. |
| 2007/0259102 A1 | 11/2007 | McNiven et al. |
| 2007/0275175 A1 | 11/2007 | Hossainy |
| 2008/0149025 A1 | 6/2008 | Swenson |
| 2008/0274266 A1 | 11/2008 | Davis et al. |
| 2009/0018643 A1 | 1/2009 | Hashi et al. |
| 2009/0090299 A1 | 4/2009 | Menendez et al. |
| 2009/0269481 A1 | 10/2009 | Chappa et al. |
| 2010/0040766 A1 | 2/2010 | Chappa et al. |
| 2010/0055294 A1 | 3/2010 | Wang et al. |
| 2010/0070020 A1 | 3/2010 | Hashi et al. |

(56) References Cited

U.S. PATENT DOCUMENTS

| | | | |
|---|---|---|---|
| 2010/0227044 A1* | 9/2010 | Scheer | 427/2.25 |
| 2011/0281019 A1 | 11/2011 | Gong et al. | |
| 2011/0281020 A1 | 11/2011 | Gong et al. | |
| 2011/0311713 A1 | 12/2011 | O'Neill et al. | |
| 2012/0100279 A1 | 4/2012 | Neumann et al. | |
| 2012/0315376 A1 | 12/2012 | Nguyen et al. | |
| 2013/0337147 A1 | 12/2013 | Chappa et al. | |
| 2014/0121597 A1 | 5/2014 | Chappa et al. | |
| 2014/0161964 A1 | 6/2014 | Chappa et al. | |
| 2014/0328998 A1 | 11/2014 | Chappa et al. | |

FOREIGN PATENT DOCUMENTS

| | | | | |
|---|---|---|---|---|
| EP | 2006-144873 | * | 5/2011 | A61F 2/06 |
| WO | 0001322 | | 1/2000 | |
| WO | 0132382 | | 5/2001 | |
| WO | 0220174 | | 3/2002 | |
| WO | 03004072 | | 1/2003 | |
| WO | 2004028579 | | 4/2004 | |
| WO | 2004028699 | | 4/2004 | |
| WO | 2004037443 | | 5/2004 | |
| WO | WO-2004037126 | | 5/2004 | |
| WO | WO-2007100801 | | 9/2007 | |
| WO | WO-2008002357 | | 1/2008 | |
| WO | 2009132214 | | 10/2009 | |
| WO | 2010024898 | | 3/2010 | |
| WO | 2010146096 | | 12/2010 | |
| WO | 2013181498 | | 12/2013 | |
| WO | 2014066760 | | 5/2014 | |
| WO | 2014182833 | | 11/2014 | |

OTHER PUBLICATIONS

Communication Pursuant to Rules 161 and 162 EPC, for European Patent Application No. 13729853.5, mailed Feb. 13, 2015 (2 pages).
Communication Pursuant to Rules 161(1) and 162 EPC, for European Application No. 13792526.9, mailed on Jul. 7, 2015 (2 pages).
Final Office Action, for U.S. Appl. No. 10/976,193, mailed Jun. 13, 2006 (10 pages).
Final Office Action, for U.S. Appl. No. 10/976,348, mailed Feb. 22, 2006 (6 pages).
International Preliminary Report on Patentability, for International Application No. PCT/US2005/038628 mailed May 10, 2007 (10 pages).
International Preliminary Report on Patentability, For PCT Application No. PCT/US2013/043547, mailed on Dec. 11, 2014 (7 pages).
International Preliminary Report on Patentability, for PCT/US2013/066810, mailed May 7, 2015 (12 pages).
International Search Report and Written Opinion, For International Application No. PCT/US2005/038628 mailed Mar. 22, 2006 (16 pages).
International Search Report and Written Opinion, For PCT Application No. PCT/US2014/037179 mailed Feb. 19, 2015 (15 pages).
International Search Report and Written Opinion, for PCT/US2013/043547, mailed Oct. 1, 2013 (10 pages).
International Search Report and Written Opinion, for PCT/US2013/066810, mailed Apr. 17, 2014 (18 pages).
Invitation to Pay Additional Fees and, Where Applicable, Protest Fee, for PCT/US2013/066810, mailed Feb. 7, 2014 (6 pages).
Invitation to Pay Additional Fees, For PCT Application No. PCT/US2014/037179, mailed on Oct. 24, 2014 (5 pages).
Non-Final Office Action, for U.S. Appl. No. 10/976,193, mailed May 17, 2007 (7 pages).
Non-Final Office Action, for U.S. Appl. No. 10/976,348, mailed Oct. 6, 2005 (13 pages).
Non-Final Office Action, for U.S. Appl. No. 11/539,443, mailed Jul. 9, 2007 (15 pages).
Non-Final Office Action, For U.S. Appl. No. 14/063,124 mailed Apr. 15, 2015 (28 pages).
Non-Final Office Action, For U.S. Appl. No. 19/906,599 mailed Apr. 9, 2015 (19 pages).
Notice of Allowance, for U.S. Appl. No. 10/976,193, mailed Mar. 8, 2011 (6 pages).
Response to Communication Pursuant to Rules 161 and 162 EPC, for European Patent Application No. 13729853.5, filed with the EPO Aug. 13, 2015 (21 pages).
Response Non-Final Office Action, for U.S. Appl. 13/906,599, mailed Apr. 9, 2015 and filed with the USPTO Aug. 10, 2015 (9 pages).
Response Non-Final Office Action, for U.S. Appl. No. 14/063,124, mailed Apr. 15, 2015 and filed with the USPTO Jul. 15, 2015 (14 pages).

* cited by examiner

COATING APPLICATION SYSTEM WITH SHAPED MANDREL

FIELD OF THE INVENTION

The invention relates to systems and methods for applying coatings to devices. More specifically, the invention relates to systems and methods for applying coatings to medical devices.

BACKGROUND OF THE INVENTION

Therapeutic benefits can be realized by administering an active agent to a subject over an extended period of time. To this end, controlled-release drug delivery systems have been developed to control the rate of drug delivery to the subject. Controlled-release drug delivery systems can include both delayed release and sustained release systems.

Site-specific drug delivery can also offer therapeutic benefits. Site-specific drug delivery refers to the delivery of an active agent to a specific target tissue site, instead of systemically. Site-specific drug delivery offers advantages because the effect of the active agent on the target tissue can be enhanced while side effects of the active agent on other tissues can be reduced.

One technique for providing controlled-release site-specific drug delivery is to use a drug-eluting coating system disposed on a medical device. The coating can serve to control the rate at which the active agent is eluted while the fact that the coating is disposed on a medical device allows delivery of the active agent to be site-specific. As an example of this approach in use, stents with drug-eluting coatings are routinely inserted into patients to prevent restenosis of the stented artery.

In some cases it can be desirable to dispose a coating only on certain portions of a medical device. For example, in some contexts, it can be desirable to dispose a coating primarily on the abluminal (outward facing) surface of a stent. However, this remains technically difficult.

SUMMARY

The invention relates to systems and methods for applying coatings to medical devices. In an embodiment the invention includes a coating apparatus including a mandrel having a lengthwise axis and an exterior surface. The exterior surface of the mandrel can define a plurality of channels disposed parallel to the lengthwise axis. The mandrel can be configured to rotate around the lengthwise axis. The coating apparatus can also include a spray head configured to direct a stream of material at the mandrel.

In an embodiment the invention includes a method of coating a medical device including positioning a medical device substrate over a mandrel, the medical device substrate having a diameter and a central lumen into which the mandrel fits. The mandrel can have a lengthwise axis and an exterior surface. The exterior surface of the mandrel can define a plurality of channels disposed parallel to the lengthwise axis. The mandrel can be configured to rotate around the lengthwise axis. The method can also include applying a stream of material to the medical device substrate, the stream having a width at the point of contact with the medical device substrate that is no more than 30 percent of the diameter of the medical device substrate.

In an embodiment the invention includes a coating apparatus including a rotation module configured to retain and rotate a cylindrical medical device and a spray head configured to generate a spray stream of material. In some embodiments the width of the spray stream at the point it contacts the cylindrical medical device is no greater than one third the diameter of the cylindrical medical device.

The above summary of the present invention is not intended to describe each discussed embodiment of the present invention. This is the purpose of the figures and the detailed description that follows.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The use of drug-eluting coating systems disposed on medical devices can offer various therapeutic advantages. Specifically, controlled-release site-specific drug delivery can be achieved, maximizing active agent concentration at a target tissue site while limiting potentially undesirable side effects on non-targeted tissue. This approach has proven successful in the context of many medical devices including coated drug-eluting stents, as the restenosis rate for coated stents has been shown to be dramatically lower than comparable bare metal stents.

In some contexts, it can be desirable to dispose a coating only on certain portions of a medical device. For example, in some contexts, it can be desirable to dispose a drug-eluting coating primarily on the abluminal (outward facing) surface of a stent with only limited amounts or none on the luminal (inward facing) surface. Current approaches to accomplish this include masking or piezoelectric ink jet techniques. However, these approaches are difficult to implement. Reasons for this include the propensity of the applied coating material to adhere the mask to the medical device substrate (e.g., forming webbing between the mask and the substrate). Defects in the coating can then be caused when the mask and the medical device are ultimately separated. In the context of piezoelectric techniques, the overall coating speed may be unacceptably slow.

Embodiments of the invention can include coating systems that can be used to apply coating materials to a particular portion of a medical device in a manner that is conducive to the integrity of the coating as well as the manufacturability of the medical device.

Applicants have discovered that the use of a mandrel having channels can influence the deposition of coating material such that a particular surface, such as the abluminal surface of a cylindrical medical device, can be preferentially coated with a coating material. While not intending to be bound by theory, it is believed that the presence of the channels can cause material that would otherwise be deflected onto the luminal or transverse surfaces to be harmlessly deposited on the mandrel.

In an embodiment the invention includes a coating apparatus including a mandrel having a lengthwise axis and an exterior surface. The exterior surface of the mandrel can define a plurality of channels disposed parallel to the lengthwise axis. The mandrel can be configured to rotate around the lengthwise axis. The coating apparatus can also include a spray head configured to direct a stream of material (spray stream) at the mandrel.

Applicants have further discovered that the ratio of the width of a spray stream to the diameter of a cylindrical medical device affects the amount of coating material that is deposited on the transverse and luminal surfaces of the medical device. Specifically, if the width of the spray stream with respect to the diameter of the medical device exceeds a certain amount, then a larger amount of the coating material will be deposited on the transverse and luminal surfaces.

In an embodiment the invention includes a coating apparatus including a rotation module configured to retain and rotate a cylindrical medical device and a spray head configured to generate a spray stream of material. In some embodiments the width of the spray stream at the point it contacts the cylindrical medical device is no greater than one third the diameter of the cylindrical medical device.

Some embodiments of the invention will now be described with reference to the figures. FIG. 1 is a schematic side view of a coating apparatus 100 in accordance with an embodiment of the invention. The apparatus 100 includes a spray head 102 attached to a support structure 108 via a mounting bracket 104. The spray head 102 can be of various types. By way of example, in some embodiments the spray head 102 can include a gas atomization type spray nozzle. An example of a suitable nozzle of this type is the SONICAIR™ nozzle, commercially available from Ivek Corporation (North Springfield, Vt.). In other embodiments, the spray head 102 can include an ultrasonic-atomization type spray nozzle. Ultrasonic nozzles are available commercially from various sources, including from Sono-Tek, Milton, N.Y. Exemplary ultrasonic nozzles are described in U.S. Pat. No. 4,978,067, the content of which is herein incorporated by reference. While not intending to be bound by theory, it is believed that ultrasonic nozzles can be advantageous in comparison to gas atomization nozzles because the divergence of the spray stream can be less. In some embodiments, the spray stream diverges less than about 10% at distances of up to 5 centimeters.

In still other embodiments the spray head 102 can include nozzles such as those commercially available from Optomec (Albuquerque, N. Mex.). Further examples of exemplary nozzles are described in U.S. Pat. No. 7,045,015, the content of which describing spray (deposition) systems is herein incorporated by reference. The spray head 102 can be in fluid communication with a pump (not shown) and a coating solution supply reservoir (not shown). While not intending to be bound by theory, spray heads such as those described in U.S. Pat. No. 7,045,015 can be advantageous because they can generate spray streams having very narrow widths with very little divergence.

The apparatus 100 also includes a rotation module 140 that includes a rotation member 114 and a mandrel 110. The mandrel can have a lengthwise axis 122 (or major axis) and can be configured to rotate around the lengthwise axis 122 (clockwise and/or counterclockwise). The mandrel can be made of various materials including metals, ceramics, polymers, and the like. In some embodiments the mandrel can be made of a porous material. In some embodiments the mandrel is stainless steel.

In operation, a medical device 112, such as a cylindrical medical device, can be disposed over the mandrel 110. Many different types of cylindrical medical devices are contemplated herein including stents, grafts, catheters, and the like. Cylindrical medical devices can include those that are substantially cylindrical. The spray head 102 can be configured to generate a stream of material 106 (or spray stream). The stream of material 106 can include a polymer, a solvent, and/or an active agent, amongst other things. The stream of material 106 can be directed at the mandrel 110 and thereby deposited onto the medical device 112. In some embodiments the spray head 102 can be configured to move along the support structure (such as with a rail mechanism) such that the material can be deposited along the length of the medical device 112. The rotation module 140 can cause the medical device 112 to be rotated such that other sides of it can be subjected to the stream of material 106. The rotation module 140 can include components such as an electric motor, gearing, and an electronic controller to control rotation of the medical device 112.

The mandrel 110 can have a plurality of channels disposed along the lengthwise axis. Referring now to FIG. 2, a schematic cross-sectional view is shown as taken along line 2-2' of FIG. 1. As shown, the medical device 112 includes a plurality of gaps separating struts (such as 132) or wires that are arranged in a circle surrounding a central lumen. The medical device 112 can have a diameter 113. The mandrel 110 includes a plurality of channels 144 and points 116. The channels 144 can be defined by the exterior surface 124 of the mandrel 110. The width of the mandrel 110 in the area of the medical device can be equal to or less than the inner diameter 113 of the medical device such that the mandrel can fit within the lumen of the medical device.

During a coating process, some amount of the stream of material 106 will impact the struts (such as 132) while some amount will pass through the gaps (such as 117) to the central lumen. Some of the material passing through to the central lumen will adhere to the mandrel 110. The channels 144 on the mandrel 110 can function to increase the relative amount of material that adheres to the mandrel surface 124 preventing it from being deflected onto the luminal (facing the lumen) and transverse surfaces of the struts. As such, the channels 144 can function to reduce the amount of material from the spray stream that is deposited on the luminal and transverse surfaces of the struts.

It will be appreciated that the precise amount of material that passes through the gaps to the central lumen is affected by the design of the medical device itself. For example, if there are more struts and/or if the gaps are narrower (a more closed design), less material would be expected to pass through the gaps. Conversely, if there are fewer struts and/or if the gaps are wider (a more open design), more material would be expected to pass through the gaps. The relative "openness" of the design can be described based on the amount of the exterior surface of the medical device that is occupied by the gaps in contrast to a cylinder having no gaps. In some embodiments, the gaps of the medical device occupy at least about 25% of the total surface area of a cylinder having the same diameter as the medical device. In some embodiments, the gaps of the medical device occupy at least about 50% of the total surface area of a cylinder having the same diameter as the medical device. In some embodiments, the gaps of the medical device occupy at least about 75% of the total surface area of a cylinder having the same diameter as the medical device. In some embodiments, the gaps of the medical device occupy at least about 90% of the total surface area of a cylinder having the same diameter as the medical device.

In some embodiments, conditions such as temperature, pressure and humidity can be controlled in the area of the spray stream and medical device substrate. For example, humidity can be controlled in any suitable manner, including at the time of preparing and/or using (as by applying) the coating composition, for instance, by coating the medical device in a confined chamber or area adapted to provide a relative humidity different than ambient conditions.

Figure 1:
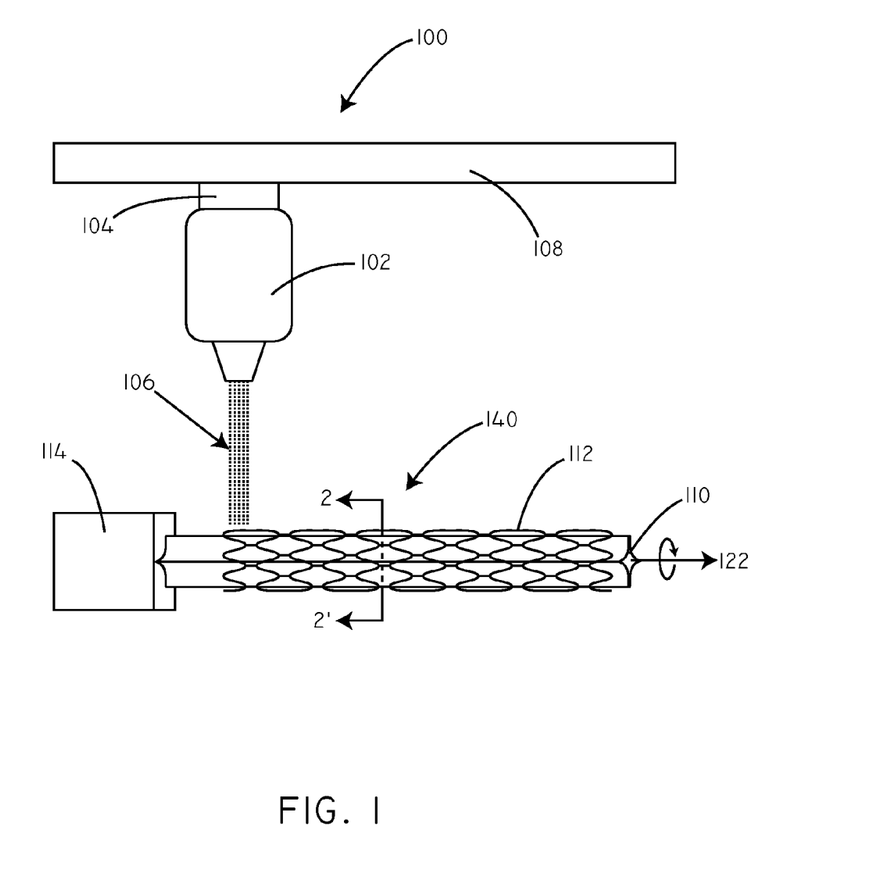
FIG. 1 is a schematic side view of a coating apparatus in accordance with an embodiment of the invention.
Figure 2:
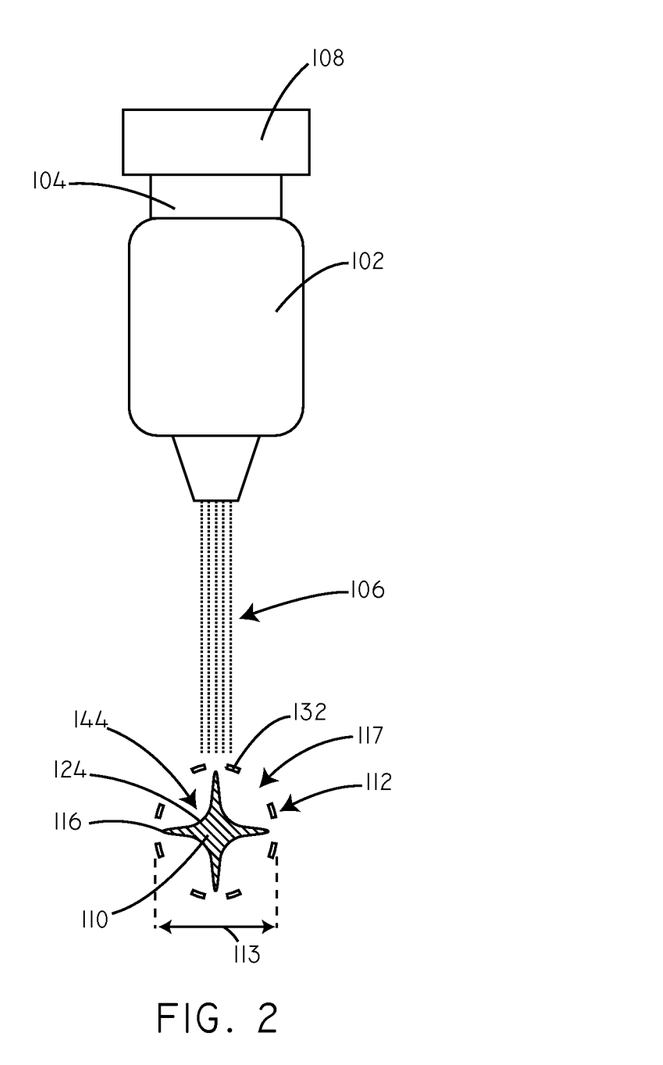
FIG. 2 is a schematic cross-sectional view of a coating apparatus as taken along line 2-2' of FIG. 1.
Figure 3:
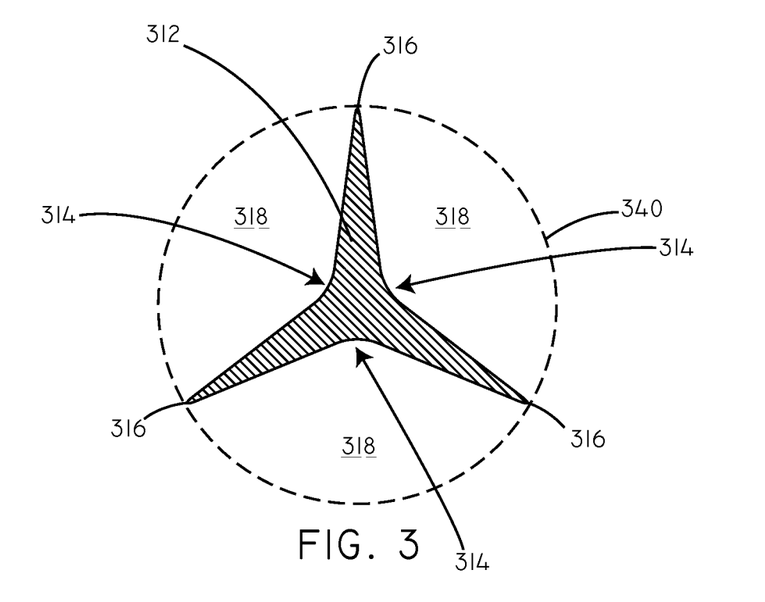
FIG. 3 is a schematic cross-sectional view of a mandrel in accordance with another embodiment of the invention.

Though the mandrel of FIG. 2 has four channels, it will be appreciated that mandrels used with embodiments herein can have various other numbers of channels. For example, FIG. 3 is a schematic cross-sectional view of a mandrel 312 in accordance with another embodiment of the invention having a different number of channels. The mandrel 312 of FIG. 3 has three channels 314 and three points 316. The channels 314 can reduce the cross-sectional area of the mandrel 312 by a significant amount in comparison to mandrels having a full circular cross-section. For purposes of illustration, a circle 340 inscribing the mandrel 312 is shown in FIG. 3. In some embodiments the cross-sectional area 318 of the channels 314 in total is at least about 40% of the area of the circle 340 inscribing the mandrel 312. In some embodiments the cross-sectional area 318 of the channels 314 in total is at least about 50% of the area of the circle 340. In some embodiments the cross-sectional area 318 of the channels in total is at least about 60% of the area of the circle 340. In some embodiments the cross-sectional area 318 of the channels 314 in total is at least about 70% of the area of the circle 340. In some embodiments the cross-sectional area 318 of the channels 314 in total is at least about 80% of the area of the circle 340. In some embodiments the cross-sectional area 318 of the channels 314 in total is at least about 90% of the area of the circle 340.

Figure 4:
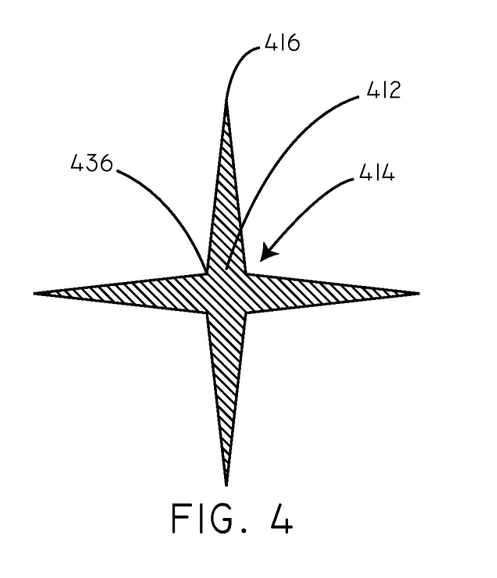
FIG. 4 is a schematic cross-sectional view of a mandrel in accordance with another embodiment of the invention.
Figure 5:
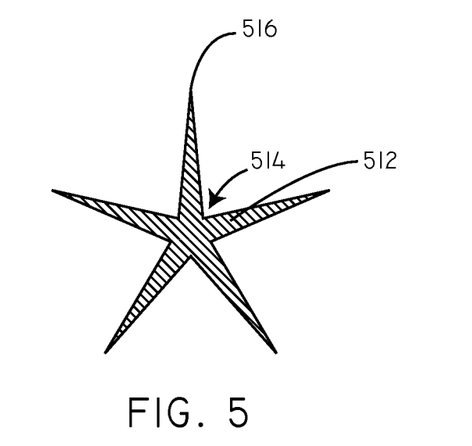
FIG. 5 is a schematic cross-sectional view of a mandrel in accordance with another embodiment of the invention.

FIG. 4 is a schematic cross-sectional view of a mandrel 412 in accordance with another embodiment of the invention. In this embodiment, the mandrel includes four channels 414 and four points 416. However, in contrast to the mandrel illustrated in FIG. 2, the inner most surface of the mandrel in the area of the channels forms a sharp angle 436 in this embodiment instead of a curve. However, many different shapes are contemplated herein. For example, the surface of the mandrel 414 in the area of the channels could be convex, parabolic, or the like. It will be appreciated that the points 416 in the embodiment of FIG. 4 have a relatively small surface area at the tip of the point (e.g., the tips of the points are relatively sharp). While not intending to be bound by theory it is believed that points having tips with a small surface area are advantageous because the contact area between such a tip and a medical device is reduced in comparison to tips that are broader. FIG. 5 is a schematic cross-sectional view of a mandrel 512 in accordance with another embodiment of the invention. In this embodiment, the mandrel 512 includes five points 516 and five channels 514.

Figure 6:
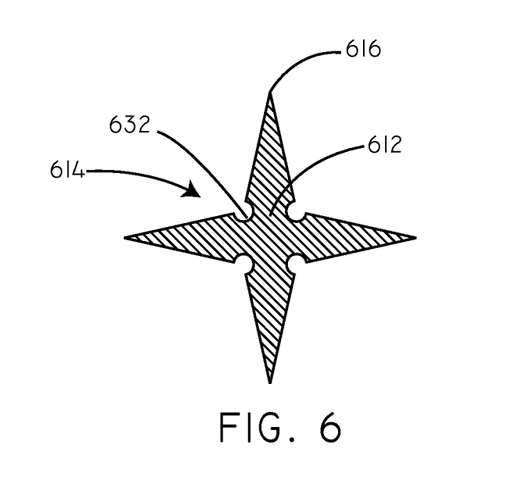
FIG. 6 is a schematic cross-sectional view of a mandrel in accordance with another embodiment of the invention.

In some embodiments, the channels may also include other features. FIG. 6 is a schematic cross-sectional view of a mandrel 612 in accordance with another embodiment of the invention. The mandrel 612 includes a plurality of points 616 and channels 614. The mandrel 612 includes an inner channel 632 at the innermost portion of each regular channel 614.

Figure 7:
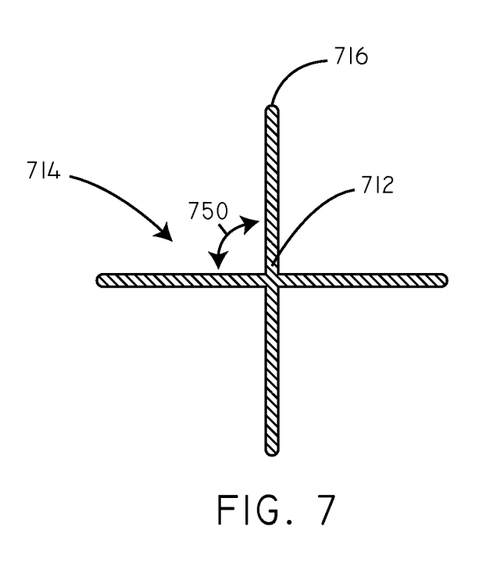
FIG. 7 is a schematic cross-sectional view of a mandrel in accordance with another embodiment of the invention.

FIG. 7 is a schematic cross-sectional view of a mandrel 712 in accordance with another embodiment of the invention. In this embodiment the mandrel 712 includes four channels 714 and four points 716. Each of the channels are each defined by two external surfaces of the mandrel 712 that are perpendicular (see right angle 750) to each other. In this embodiment, the mandrel has the shape of an 'X' in cross-section.

Figure 8:
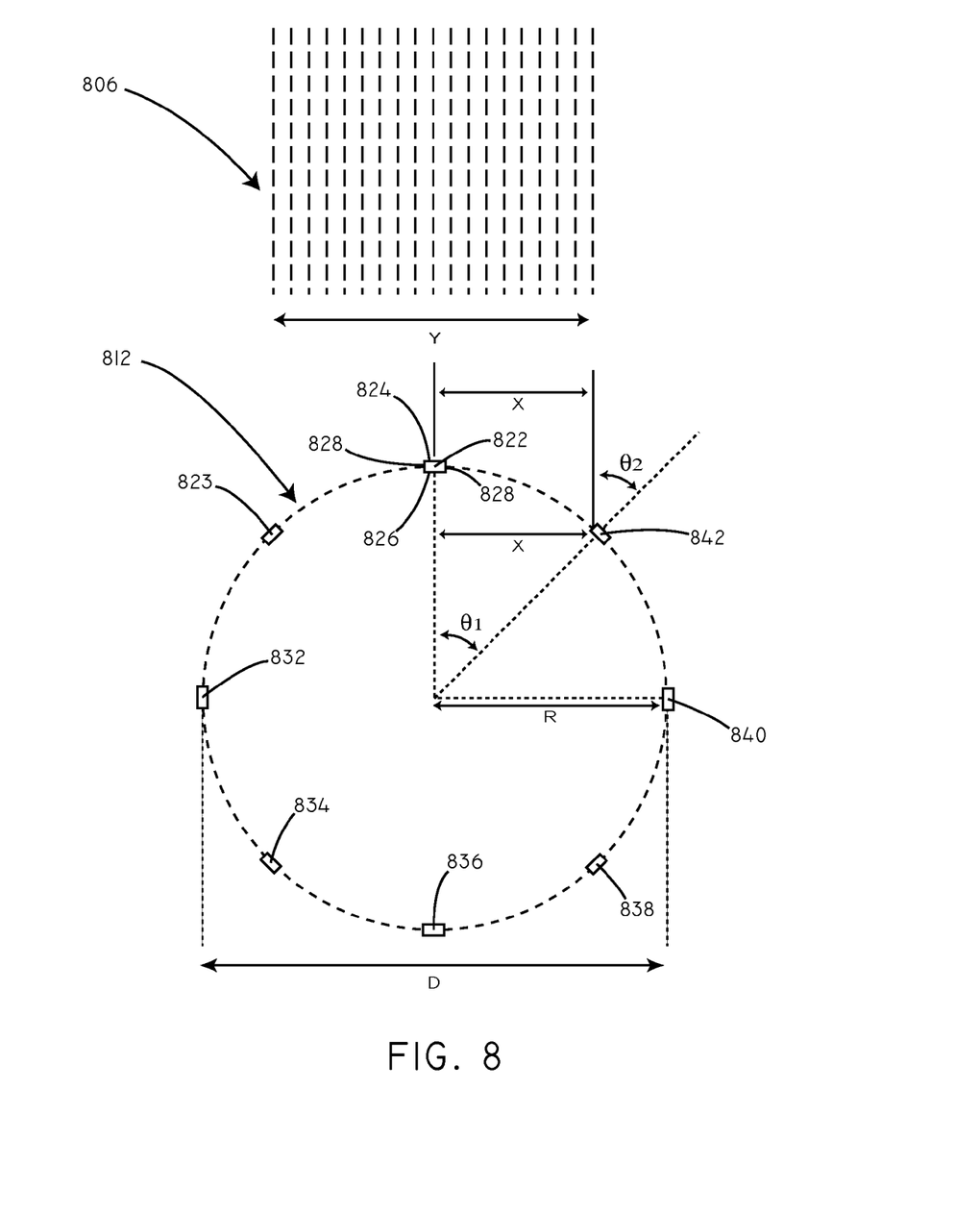
FIG. 8 is a schematic cross-sectional view illustrating how a spray stream can impact a substrate in accordance with an embodiment of the invention.
Figure 9:
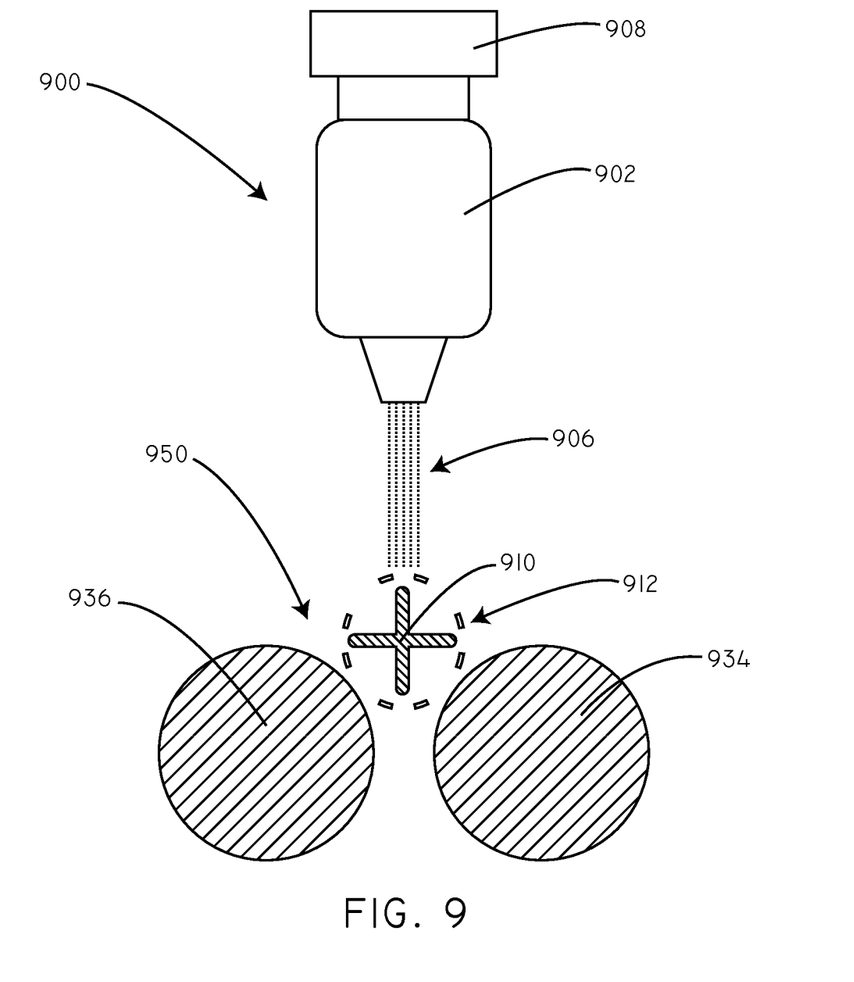
FIG. 9 is a schematic cross-sectional view of a coating apparatus in accordance with another embodiment of the invention.

FIG. 8 is a schematic cross-sectional view illustrating how a spray stream 806 can impact a substrate in accordance with an embodiment of the invention. In this example a spray stream 806 is shown as it is applied to a medical device 812. The spray stream 806 is centered over the medical device 812. The spray stream 806 has a width Y. The medical device includes a plurality of struts 822, 823, 832, 834, 836, 838, 840, and 842. It will be appreciated that medical devices may also have different numbers of struts and with different shapes. Each strut (as illustrated with respect to strut 822) includes a luminal surface 826, an abluminal surface 824, and transverse surfaces 828. Angle $\theta_2$ describes the angle of incidence for spray material that impacts the uppermost transverse surface of strut 842. Angle $\theta_2$ is equal to angle $\theta_1$ and as such angle $\theta_2$ is equal to the arcsine of X divided by the radius R of the medical device.

$$\theta_2 = ARCSINE(X/R)$$

As such, if spray material traveling straight downward impacts the upper most transverse surface of a strut at a lateral distance (X) of 0.1 mm from the lateral center of the device which has a radius (R) of 1 mm, the angle of incidence of the spray material with respect to the transverse surface will be 5.74 degrees. Similarly, if spray material traveling straight downward impacts the upper most transverse surface of a strut at a lateral distance (X) of 0.5 mm from the lateral center of the device which has a radius (R) of 1 mm, the angle of incidence of the spray material with respect to the transverse surface will be 30 degrees. Table 1 below illustrates the angle of incidence $\theta_2$ of spray material onto the transverse surface of a strut as a function of the relative values of X (half the width of the spray stream centered over the medical device) to R (the radius of the medical device.

TABLE 1

| X | R | X/R Ratio | $\theta_2$ |
|---|---|---|---|
| 0.0 | 1 | 0.0 | 0.00 |
| 0.1 | 1 | 0.1 | 5.74 |
| 0.17 | 1 | 0.1 | 10.00 |
| 0.2 | 1 | 0.2 | 11.54 |
| 0.3 | 1 | 0.3 | 17.46 |
| 0.4 | 1 | 0.4 | 23.58 |

TABLE 1-continued

| X | R | X/R Ratio | $\theta_2$ |
|---|---|---|---|
| 0.5 | 1 | 0.5 | 30.00 |
| 0.6 | 1 | 0.6 | 36.87 |
| 0.7 | 1 | 0.7 | 44.43 |
| 0.8 | 1 | 0.8 | 53.13 |
| 0.9 | 1 | 0.9 | 64.16 |
| 1.0 | 1 | 1.0 | 90.00 |

Figure 10:
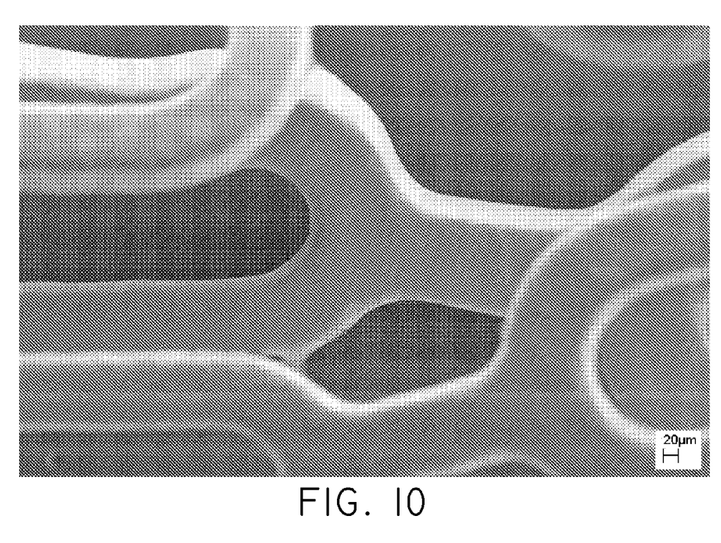
FIG. 10 is scanning electron microscopy (SEM) image of surfaces of a stent.

It has been found that the greater the angle of incidence of material with respect to the transverse surface of the struts, the more likely that the material will contact and adhere to the transverse surface of the strut. As such, the amount of material deposited on the abluminal surface with respect to the amount deposited on other surfaces can be maximized by controlling the width of the spray stream. In some embodiments, the apparatus is configured such that the width of the spray stream (Y) is no greater than one third the diameter (D) of the medical device (Y/D ratio no greater than 0.33). Stated alternately, the apparatus is configured such that the half width of the spray stream (X) is no greater than one third the radius (R) of medical device (the (Y/D ratio is equal to the X/R ratio). In some embodiments the Y/D ratio (or X/R ratio) is no greater than 0.25.

While not intending to be bound by theory, it believed that when the angle of incidence is below 10 degrees, substantially no coating material is deposited on the transverse surfaces of the strut. As shown in Table 1 above, an angle of incidence of 10 degrees corresponds to an X/R (or Y/D) ratio of approximately 0.17. As such, in some embodiments the width of the coating stream is no greater than about 0.17 of the diameter of the medical device to be coated (e.g., the Y/D ratio or X/R ratio is no greater than 0.17).

In some embodiments, the rotation module can include components in addition to a mandrel. By way of example, FIG. 9 is a schematic cross-sectional view of a coating apparatus 900 in accordance with another embodiment of the invention. The coating apparatus 900 includes a support structure 908 and a spray head 902. The spray head 902 creates a stream of material 906. The apparatus 900 includes a rotation module 950. The rotation module 950 includes a mandrel 910 and a pair of rollers including a first roller 934 and a second roller 936. A medical device 912 is disposed around the mandrel 910. The mandrel 910 can function to keep the medical device 912 positioned between the rollers 934, 936. The rollers 934, 936 can be used to aid in rotating the medical device 912. The coating apparatus 900 can also include components as described in U.S. Pub. App. Nos. 2003/0190420, 2004/0062875, 2004/0194704, 2005/0158449, 2006/0088653 and 2006/0165872, the contents of all of which are herein incorporated by reference in their entirety.

It will be appreciated that embodiments herein can include various methods, such as various methods for coating a medical device. In an embodiment, a method of coating a medical device is included that includes positioning a medical device substrate over a mandrel. The medical device substrate can have a diameter and a central lumen into which the mandrel fits. The mandrel can have a lengthwise axis and an exterior surface. The exterior surface of the mandrel can define a plurality of channels disposed parallel to the lengthwise axis. The mandrel can be configured to rotate around the lengthwise axis. The method can also include applying a stream of material to the medical device substrate, the stream having a width at the point of contact with the medical device substrate that is no more than 30 percent of the diameter of the medical device substrate.

In some embodiments of the method, at least about 80 percent of the total amount of material deposited on the medical device substrate is deposited on an abluminal surface. In some embodiments of the method, at least about 90 percent of the total amount of material deposited on the medical device substrate is deposited on an abluminal surface. In some embodiments of the method, at least about 95 percent of the total amount of material deposited on the medical device substrate is deposited on an abluminal surface.

While various exemplary embodiments herein have been described with respect to applying a coating on to a stent, it will be appreciated that such embodiments can also be applied to many other types of medical devices, including many other types of cylindrical medical devices.

The present invention may be better understood with reference to the following examples. These examples are intended to be representative of specific embodiments of the invention, and are not intended as limiting the scope of the invention.

EXAMPLES

Example 1

Application of a Coating onto the Abluminal Surface of Stents

A plurality of stainless steel ORBUS R™ stents having an inside diameter of approximately 1.5 mm were obtained from OrbusNeich (Ft. Lauderdale, Fla.). A coating composition was formed by dissolving a polymer consisting of polylactic and glycolic acid constituents into acetone.

The stents were divided into four different test groups. The coating composition was applied to the first test group with an ultrasonic spray nozzle (SONO-TEK, Milton N.Y.) while the stents were held in place between two rollers (as described in U.S. Publ. Pat. App. No. 2007/0101933) without using a mandrel in the lumen of the stents. The spray stream created by the spray nozzle had a width of approximately 0.9 mm at the point of impact with the medical device ($\theta_2 \approx 36.9$ degrees). The stents were inspected after the coating procedure using scanning electron microscopy and optical interferometry to measure thickness. Specifically, images of the coated stents were made using a Leo 1550VP Field Emission Scanning Electron Microscope (Leo Electronic Systems, Cambridge, U.K.). Briefly, the instrument uses a low voltage electron beam to scan only the outer surface of a sample, penetrating typically less than 10 nm. This technique provides excellent visual contrast for stents between the bare metal and the polymer coated surfaces due to electron scattering. Thickness measurements were made using a Veeco NT1100 Optical Profiler (Veeco Instruments, Inc., Plainview, N.Y.). The instrument uses interference fringes to measure 3D surface profiles with nanometer precision in the Z direction (height). Using the thickness analysis option in the software, transparent coatings can be measured by subtracting the coating surface profile from the stent surface profile. The difference results in a thickness profile of the coating down to a minimum thickness of approximately 2 μm. Below 2 μm, the optical profiler software is unable to resolve the overlapping interferograms. However, if spots of bare metal are visible, the SEM can be used to zoom in on the edges of the coating and approximate the coating thickness with a relatively high level of accuracy.

FIG. 10 shows an SEM image of the luminal, abluminal, and transverse surfaces of the stent in the first test group. As can be seen, all surfaces of the stent were coated with the polymer composition. Thickness measurements made using the optical profiler show that inner diameter was only slightly thinner than the outer diameter. It was estimated that approximately 60 percent of the total amount of coating material deposited onto the stents was deposited onto the abluminal surface whereas approximately 40 percent of the coating material was deposited on other surfaces (luminal and transverse surfaces) of the stents.

The coating composition was applied to the second test group with an ultrasonic spray nozzle (SONO-TEK, Milton N.Y.) while the stents were held in place between two rollers (as described in U.S. Publ. Pat. App. No. 2007/0101933) with a mandrel having a circular cross-section (e.g., round mandrel, diameter of 1.397 mm). The spray stream created by the spray nozzle had a width of approximately 0.9 mm at the point of impact with the medical device ($\theta_2 \approx 36.9$ degrees). The coated stents were again inspected using scanning electron microscopy and optical interferometry.

Figure 11:
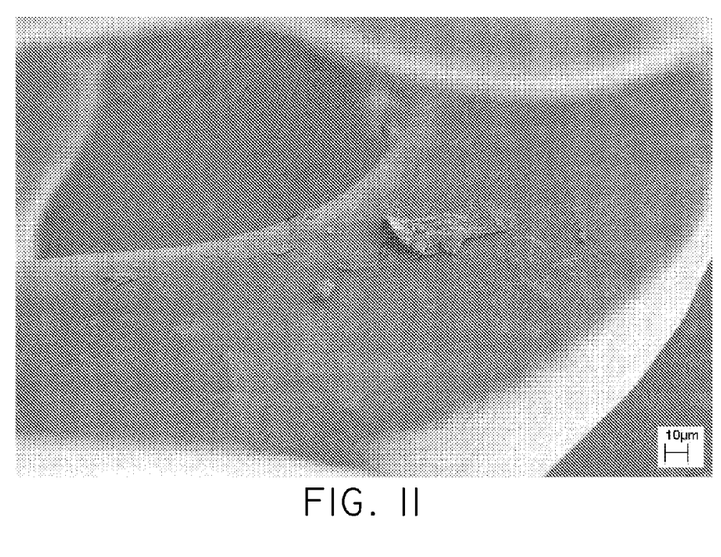
FIG. 11 is scanning electron microscopy (SEM) image of surfaces of a stent.

FIG. 11 shows an SEM image of the luminal and transverse surfaces of the stent in test group two. All surfaces of the stent were coated with the polymer composition. However, the coating on the luminal surface was below the threshold of the optical profiler (less than 2 µm). Defects in the coating (including peeling) were observed on the luminal surface of the stent as shown in FIG. 11.

The coating composition was applied to the third test group with an ultrasonic spray nozzle identical to the one used for the first and second test groups using the same settings. Again, the stents were held in place between two rollers. The spray stream created by the spray nozzle had a width of approximately 0.9 mm at the point of impact with the medical device ($\theta_2 \approx 36.9$ degrees). However, the mandrel used to hold the stents in place for the third group had a cross-sectional shape similar to the mandrel depicted in FIG. 2. The mandrel had a diameter (maximum distance point to opposite point) of 1.397 mm).

Figure 12:
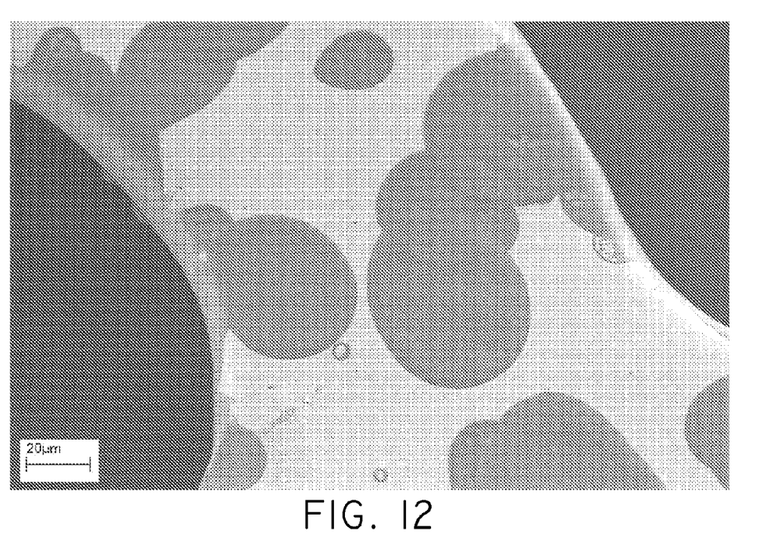
FIG. 12 is scanning electron microscopy (SEM) image of surfaces of a stent.

The stents were again inspected using scanning electron microscopy and optical interferometry. FIG. 12 shows an SEM image of the luminal surfaces of the stent. As can be seen, there were many regions of the luminal surface that were completely uncoated. The thickness of the coating on the abluminal surface was measured to be between 4.0 and 6.0 µm. It was estimated that approximately 80 percent or more of the total amount of coating material deposited onto the stent was deposited onto the abluminal surface whereas no more than 20 percent of the coating material was deposited on other surfaces of the stent.

The coating composition was applied to the fourth test group with an Optomec M3D spray nozzle/system (Optomec, Albuquerque, N. Mex.). The spray stream created by the spray nozzle had a width of approximately 0.1 mm at the point of impact with the medical device ($\theta_2 \approx 3.8$ degrees). The mandrel used to hold the stents in place for the fourth group had a cross-sectional shape similar to the mandrel depicted in FIG. 2. The mandrel had a diameter (maximum distance point to opposite point) of 1.397 mm).

Figure 13:
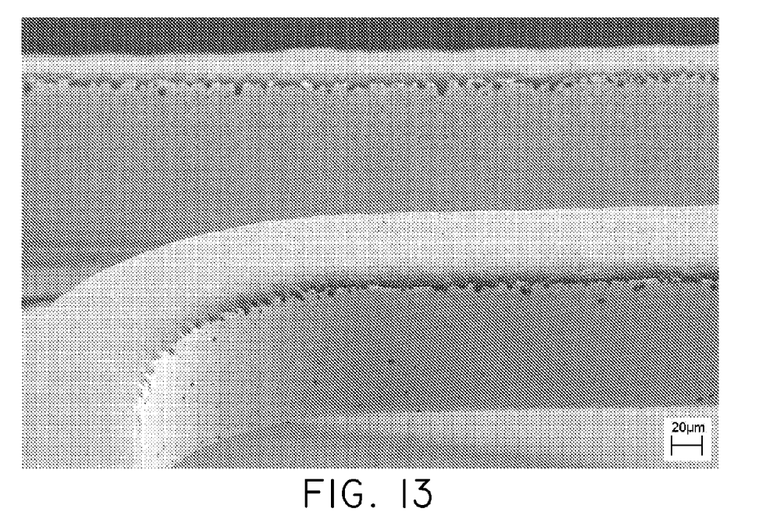
FIG. 13 is scanning electron microscopy (SEM) image of surfaces of a stent.

The stents were again inspected using scanning electron microscopy and optical interferometry. FIG. 13 shows an SEM image of the abluminal and transverse surfaces of the stent. It was observed that there was virtually no coating material on the transverse and luminal surfaces of the stent. The thickness of the coating on the abluminal surface was measured to be between 4.0 and 6.0 µm. It was estimated that approximately 95 percent or more of the total amount of coating material deposited onto the stent was deposited onto the abluminal surface whereas no more than 5 percent of the coating material was deposited on other surfaces of the stent.

This example shows that mandrels with channels can be effective to reduce the amount of coating material that is deposited onto transverse and luminal surfaces of a medical device during a coating process. This example further shows that coating apparatus with narrow spray streams can be effective to reduce the amount of coating material that is deposited onto transverse and luminal surfaces of a medical device during a coating process.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific embodiments and techniques. However, it should be understood that many variations and modifications may be made while remaining within the spirit and scope of the invention.

The invention is claimed is:

1. A coating apparatus comprising:
    a rotation module configured to retain and rotate a cylindrical medical device having a luminal surface, an abluminal surface and a diameter, the rotation module comprising a mandrel having a lengthwise axis and an exterior surface, the exterior surface of the mandrel defining a plurality of channels disposed parallel to the lengthwise axis, the mandrel configured to rotate around the lengthwise axis; and
    a spray head configured to generate a spray stream of coating material having a width, wherein the width of the spray stream where it contacts the cylindrical medical device is no greater than one third the diameter of the cylindrical medical device, wherein the channels on the mandrel and the width of the spray stream cause the abluminal surface of the cylindrical medical device to be preferentially coated with the coating material with limited amounts of coating material deposited on the luminal surface of the cylindrical medical device.

2. The coating apparatus of claim 1, the mandrel comprising between three and ten channels.

3. The coating apparatus of claim 1, each of the channels defined by a portion of the mandrel that is convex in cross-section.

4. The coating apparatus of claim 1, the mandrel having a star shape in cross-section with between three and nine points.

5. The coating apparatus of claim 1, the channels comprising at least about 50% of the cross-sectional volume of a circle inscribing the mandrel.

6. The coating apparatus of claim 1, the mandrel configured to be disposed within the lumen of a cylindrical medical device.

7. The coating apparatus of claim 1, further comprising a rotation member coupled to the mandrel, the rotation member configured to rotate the mandrel around the lengthwise axis.

8. The coating apparatus of claim 1, further comprising a first roller and a second roller both disposed parallel to the lengthwise axis of the mandrel.

9. The coating apparatus of claim 1, further comprising a first roller and a second roller both disposed parallel to the lengthwise axis of the mandrel.

10. The coating apparatus of claim 1, the first roller and second roller separated by a gap of less than about 1 centimeter, the mandrel disposed directly above the center of the gap.

11. The coating apparatus of claim 1, the mandrel comprising a porous material.

12. The coating apparatus of claim 10, the spray head configured to generate a spray stream of material that diverges less than 10% at distances of less than five centimeters.

13. The coating apparatus of claim 10, the spray head configured to generate a spray stream of material with a width of no greater than 100 µm at the point it contacts the cylindrical medical device.

14. The coating apparatus of claim 1, the width of the spray stream at the point it contacts the cylindrical medical device no greater than one quarter the diameter of the cylindrical medical device.

15. The coating apparatus of claim 1, the rotation module comprising a mandrel, the surface of the mandrel defining a plurality of channels disposed parallel to the major axis of the mandrel.

16. The coating apparatus of claim 1, wherein the spray stream of material has an angle of incidence below 10 degrees.

* * * * *